United States Patent
Osa et al.

(10) Patent No.: US 10,743,927 B1
(45) Date of Patent: Aug. 18, 2020

(54) ANCHOR BOLT DRIVER DEVICE

(71) Applicant: PMT Corporation, Chanhassen, MN (US)

(72) Inventors: Benjamin Osa, Minneapolis, MN (US); Charles Talbott, St. Paul, MN (US)

(73) Assignee: PMT Corporation, Chanhassen, MN (US)

( * ) Notice: Subject to any disclaimer, the term of this patent is extended or adjusted under 35 U.S.C. 154(b) by 147 days.

(21) Appl. No.: 16/190,372

(22) Filed: Nov. 14, 2018

Related U.S. Application Data

(63) Continuation-in-part of application No. 15/171,221, filed on Jun. 2, 2016, now abandoned.

(60) Provisional application No. 62/169,894, filed on Jun. 2, 2015.

(51) Int. Cl.
*A61B 17/88* (2006.01)
*A61B 17/00* (2006.01)

(52) U.S. Cl.
CPC ........ *A61B 17/8888* (2013.01); *A61B 17/888* (2013.01); *A61B 2017/00867* (2013.01)

(58) Field of Classification Search
CPC ................. A61B 17/888; A61B 17/8888
See application file for complete search history.

(56) References Cited

U.S. PATENT DOCUMENTS

| | | | | |
|---|---|---|---|---|
| 4,242,932 A * | 1/1981 | Barmore | ........... | F16B 23/0092 411/403 |
| 5,249,899 A * | 10/1993 | Wilson | ........... | B25B 13/06 411/258 |
| 5,520,075 A * | 5/1996 | Barmore | ........... | B25B 13/06 81/437 |
| 10,495,127 B2 * | 12/2019 | Nielson | ........... | F16B 23/0007 |
| 2003/0105471 A1 * | 6/2003 | Schlapfer | ........... | B25B 23/108 606/104 |
| 2004/0225292 A1 * | 11/2004 | Sasso | ........... | A61B 17/8816 606/916 |
| 2005/0277940 A1 * | 12/2005 | Neff | ........... | A61B 17/8625 606/916 |
| 2012/0247284 A1 * | 10/2012 | Murray | ........... | A61B 17/888 81/436 |
| 2013/0030476 A1 * | 1/2013 | Shimko | ........... | A61B 17/8615 606/308 |
| 2017/0238982 A1 * | 8/2017 | Alicastro | ........... | A61B 17/8615 |
| 2018/0280067 A1 * | 10/2018 | Bjork | ........... | A61B 17/888 |

* cited by examiner

*Primary Examiner* — Nicholas W Woodall
(74) *Attorney, Agent, or Firm* — Eggink & Eggink; Anthony G. Eggink; Katrina M. Eggink

(57) ABSTRACT

An anchor bolt driver device for fixing and removing anchor bolts utilized in neurosurgery. The anchor bolt driver device has a handle portion and a shaft extending therefrom. A socket of a predetermined configuration is formed at the terminal end of the shaft and a pin structure having a predetermined configuration extends outward and axially through the socket. The socket and pin structure are constructed and arranged to receive an anchor bolt for the threading engagement with the skull of a patient.

20 Claims, 5 Drawing Sheets

ANCHOR BOLT DRIVER DEVICE

This application is a Continuation-in-Part of U.S. patent application Ser. No. 15/171,221, filed on Jun. 2, 2016, which claims the benefit of U.S. Provisional Patent Application No. 62/169,894, filed on Jun. 2, 2015, and both of which being incorporated in its entirety by reference herein.

The present invention relates generally to an anchor bolt driver device and particularly to a device for fixing and removing anchor bolts in the skull of a patient for subsequent catheter and neurosurgery electrode placement, for example. More particularly, the invention relates to an anchor bolt driver device constructed for use with a stereotactic frame.

BACKGROUND OF THE INVENTION

Various stereotactic devices used in neurosurgery utilize burr hole mounted systems which use anchor bolts threaded into the skull of a patient. The anchor bolt driver device of the present invention is constructed to engage and rotate the anchor bolts for insertion and removal in cooperation with a stereotactic frame.

Anchor bolt drivers are known, however various issues, difficulties and limitations still exist relating to anchor bolt drivers that are placed through a lumen of the bushing of a stereotactic frame which are typically vertical or nearly vertical in position. When the shaft of the anchor bolt driver travels through the stereotactic lumen to reach past its distal end adjacent the patient's skull, the doctor or other personnel needs to position the anchor bolt into the driver's socket. Typically little space exists between the distal tip of the stereotactic lumen and the patient's skull, thereby making the attachment process cumbersome, ergonomically awkward, and sometimes not possible due to the tight space constraints.

Having a socket that is a press fit on the anchor bolt driver's drive head may work as a short term solution but it is problematic to maintain tolerances of both the driver's socket and the anchor bolt. Additionally, for small scale drive heads that are only one or two millimeters in size, for example, the socket of the driver often wears quickly thereby loosening up the press fit mating feature between the socket and the drive head of the anchor bolt.

In summary, prior art anchor bolt drivers do not provide a consistent means to attach the anchor bolt to the driver socket for ease of use in a stereotactic process. The state of the art for bone screws or anchor bolts for human use is typically nonferrous material such as titanium or a polymer such as PEEK. These screws and bolts are typically non-magnetic so a magnetic socket is not an option for use.

The anchor bolt driver design of the present invention overcomes the shortcomings and limitations of the prior art. Further, because the structure is a one piece design, it makes sterilization via steam autoclave or STERRAD easier because health care professionals do not need to take apart the driver and thus do not need to reassemble it.

SUMMARY OF THE INVENTION

An anchor bolt driver device for fixing and removing anchor bolts utilized in neurosurgery. The anchor bolt driver device has a handle portion and a shaft extending therefrom. A socket of a predetermined configuration is formed at the terminal end of the shaft and a pin structure having a predetermined configuration extends outward and axially through the socket. The socket and pin structure are constructed and arranged to receive an anchor bolt for the threading engagement with the skull of a patient.

The anchor bolt driver of the invention comprises a pin that has a predetermined pin shape that once the anchor bolt is slid onto the pin and pushed into the drive socket (which is typically a square but also could be a hex, starburst, or triangular in cross section), the anchor bolt is held within the socket by the forces of the pin springing out of shape slightly since the amplitude of the bend is slightly larger than the radius of the lumen of the anchor bolt or the skull screw having an inner lumen. Even if the anchor bolt's drive head is not a press fit in the drive socket, the pin will hold the anchor bolt it place securely even if the anchor bolt is hanging vertically. The pin of the driver is also designed so the anchor bolt's linear axis is concentric with the shaft of the anchor bolt driver. The anchor bolt driver device configuration is ideal for keeping the trajectory of the anchor bolt in line with the angle in which the burr hole was drilled utilizing a stereotactic frame.

The anchor bolt driver is a reusable tool that can be sterilized via STERRAD or steam autoclaving. The shape of the pin allows for ease of cleaning using a cleaning wipe and the anchor bolt driver is a unitary one piece design. The anchor bolt driver's shaft is a similar diameter as the anchor bolt and the drill bit used to create a burr hole in the skull. This allows the same size stereotactic lumen to accept the introduction and passing through of these three items. This speeds up the process of the surgery, saving money since minutes in the operating room are very expensive. The alternative would be to alternate between different bushings with different lumens or have a reducing bushing to add and remove for the drilling process. The latter adds time and may also reduce the accuracy of the stereotactic procedure.

Using the anchor bolt driver of the present invention, the stereotactic procedure consists of the following steps:
1. Drilling a hole in the patient's skull by first placing the drill through the lumen of the stereotactic bushing.
2. Removing the drill from the bushing.
3. Pushing the anchor bolt onto the anchor bolt driver's pin until the drive head on the anchor bolt is mating with the drive socket of the driver.
4. Inserting the anchor bolt driver with the anchor bolt attached through the lumen of the stereotactic bushing and screwing the self tapping anchor bolt into the skull.
5. Pulling out the anchor bolt driver from the lumen of the stereotactic bushing. This process also disengages the socket from the drive head of the anchor bolt.

These and other benefits of this invention will become clear from the following description by reference to the drawings.

DESCRIPTION OF THE PREFERRED EMBODIMENTS

Figure 1:
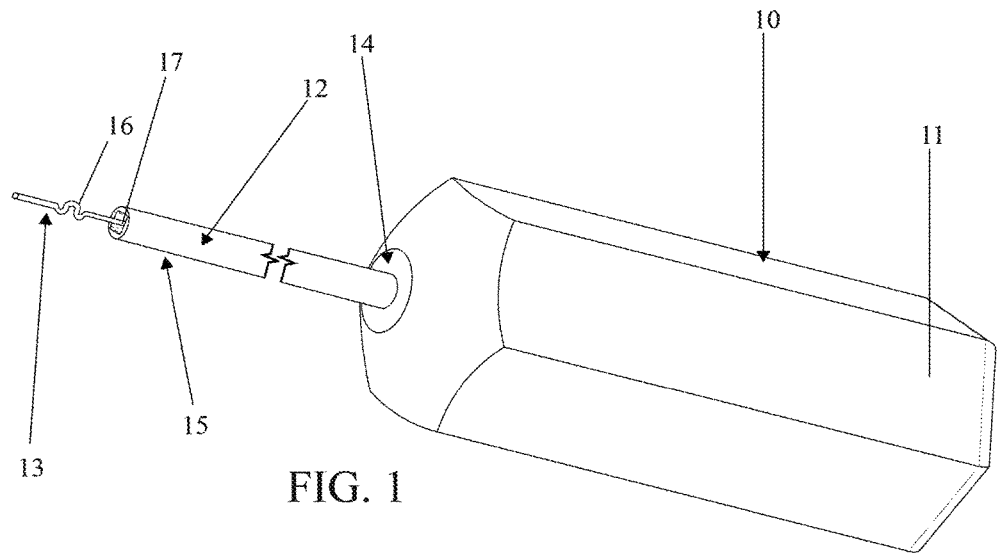
FIG. 1 is a perspective view showing the anchor bolt driver device of the invention.

As shown in FIG. 1, the anchor bolt driver device 10 is shown having a handle portion 11, a shaft 12 extending from the handle portion 11 and a formed pin 13 extending from the shaft 12. The shaft 12 may be of any desired length. The terminal end of the shaft 12 is shown to have a formed socket 17 and through which the formed pin 13 extends. The formed pin structure 13 is shown fixed within the socket 17 of shaft 12 at connection 15, for example. Connection 15 may be in hole 42 in the rear wall 41 of the cavity formed into socket 17. The shaft 12 may have a length of approximately 6.25 inches, for example, but may be shorter or longer depending upon the length requirement of the stereotactic equipment, for example, as further discussed with respect to FIGS. 6A-6G.

Figure 2:
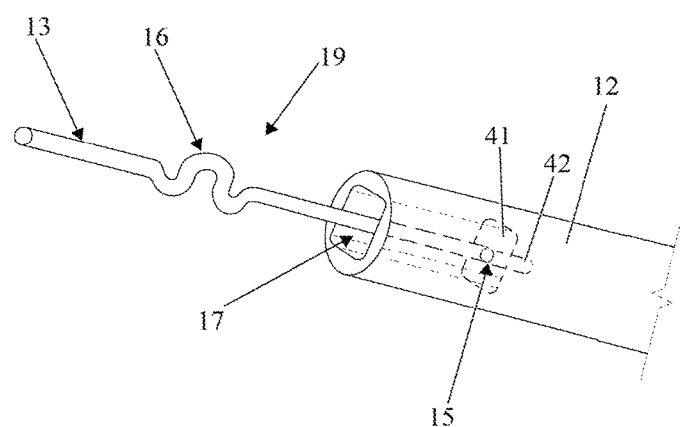
FIG. 2 is an enlarged perspective view of FIG. 1 and showing the shaft and formed pin structure extending therefrom.
Figure 2A:
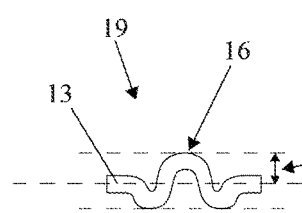
FIG. 2A is an enlarged view of the bend in the formed pin structure shown in FIG. 2.
Figure 3:
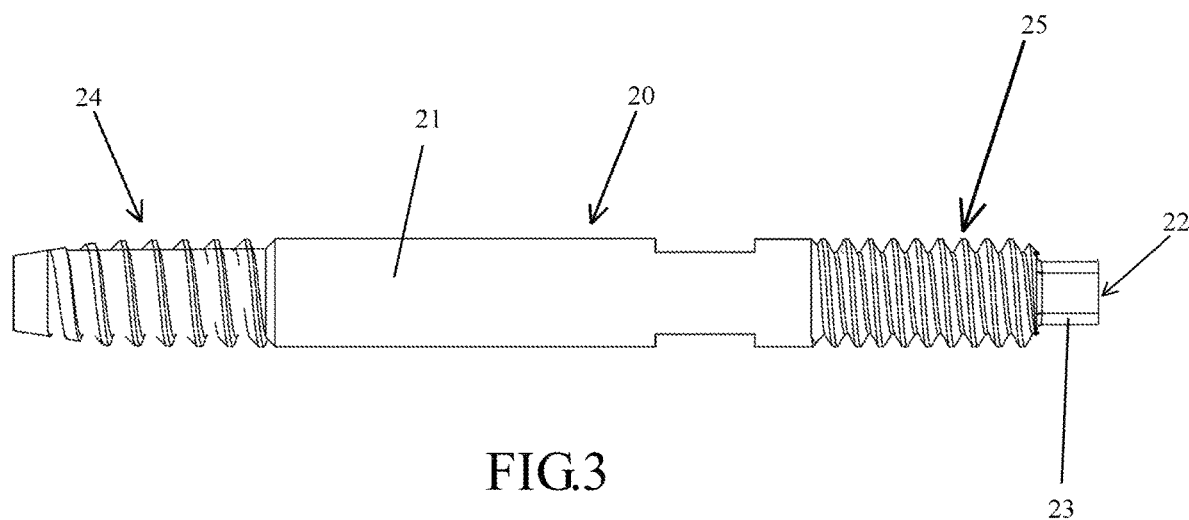
FIG. 3 is a plan view of an anchor bolt.
Figure 4:
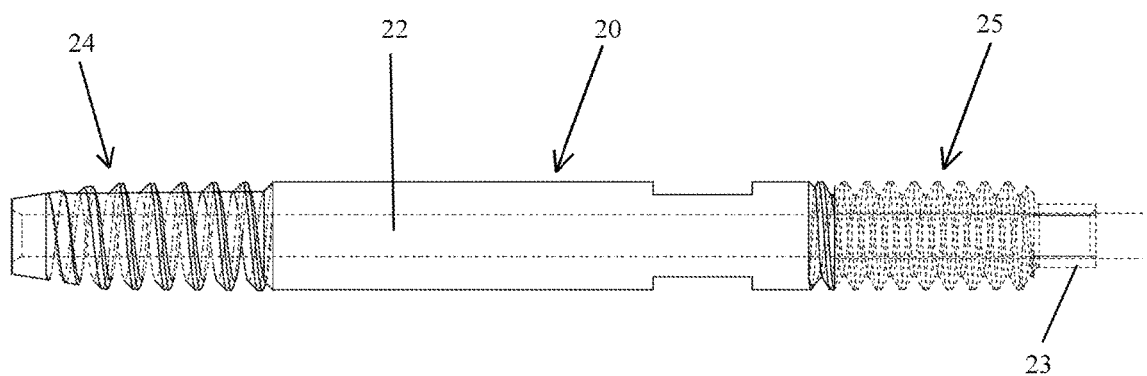
FIG. 4 is another plan view of the anchor bolt of FIG. 3.
Figure 5:
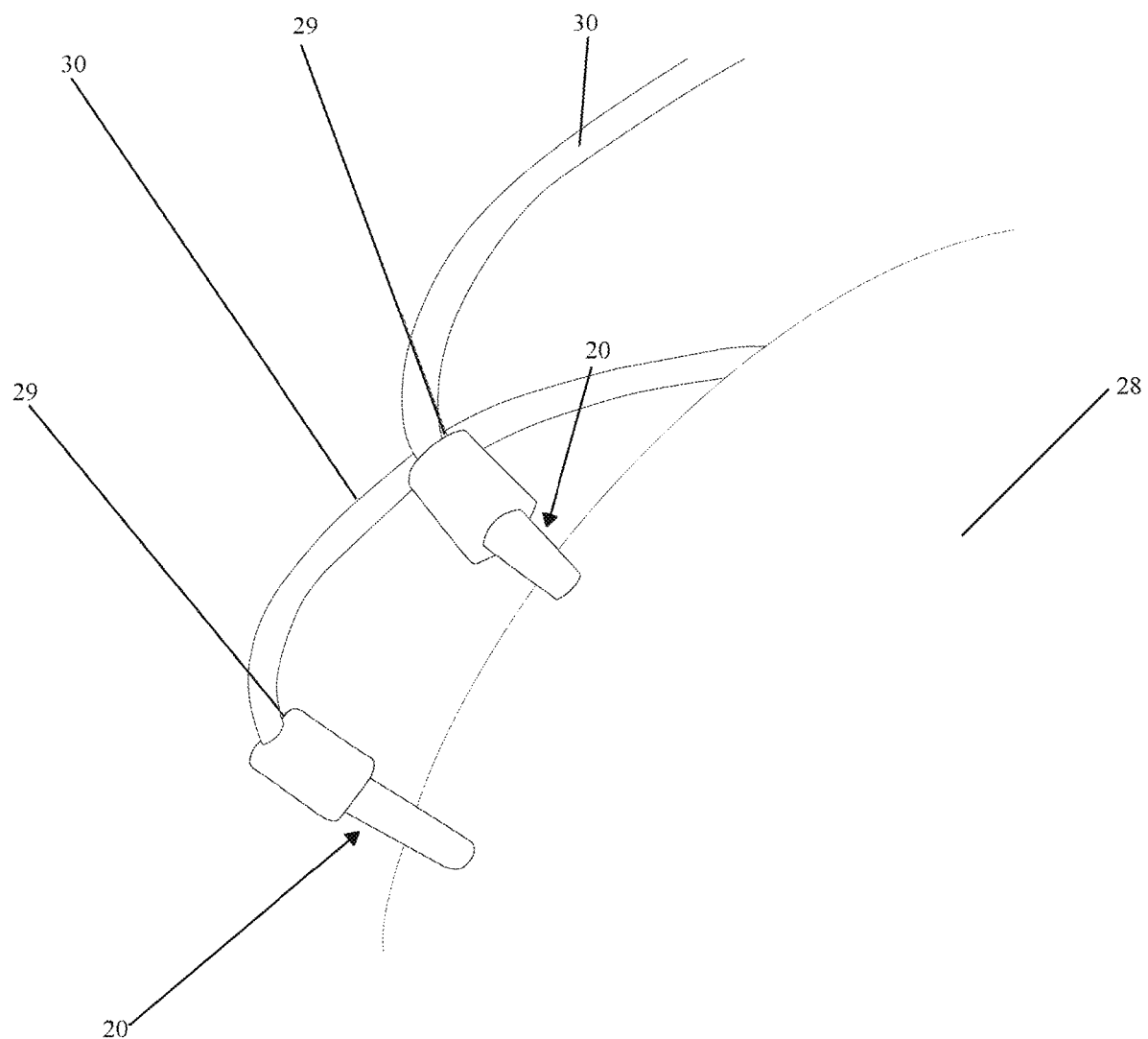
FIG. 5 is a perspective view showing anchor bolts positioned in the skull of a patient.
Figure 6A:
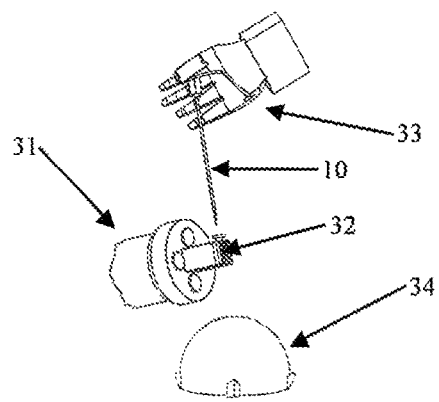
FIGS. 6A-6G are perspective views showing the anchor bolt driver device of the present invention utilized in a stereotactic frame to thread an anchor bolt into a burr hole in a skull.
Figure 6B:
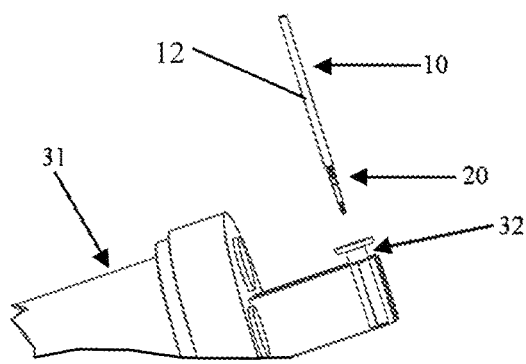
Figure 6C:
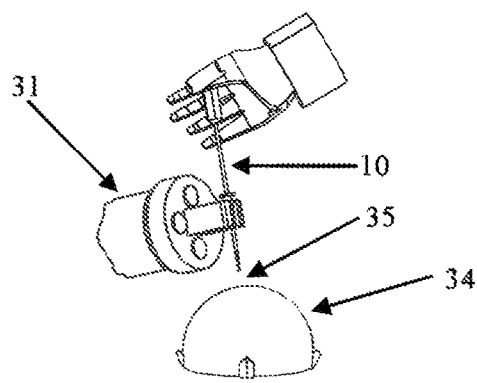
Figure 6D:
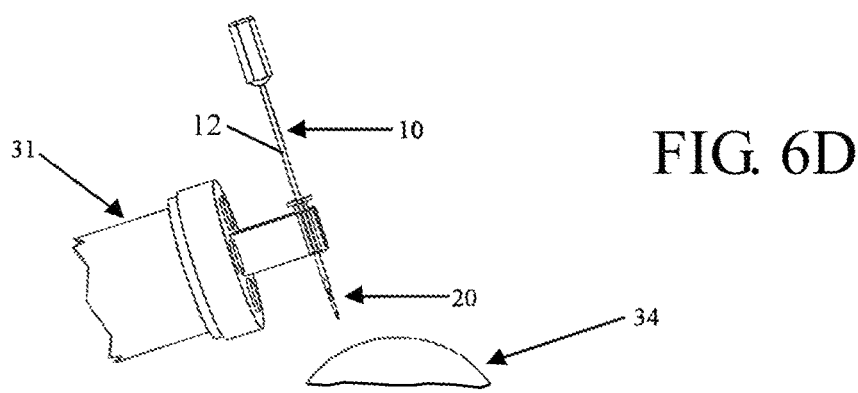
Figure 6E:
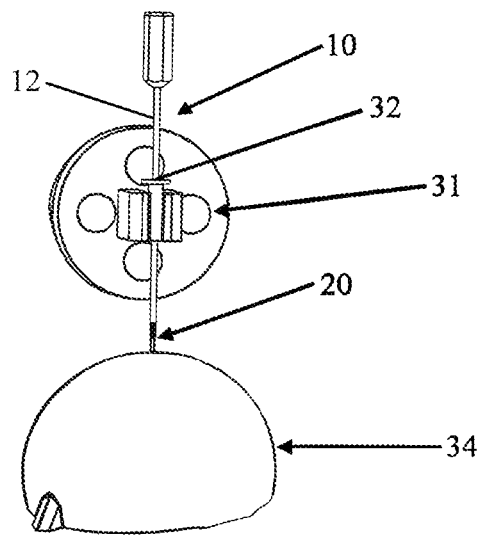
Figure 6F:
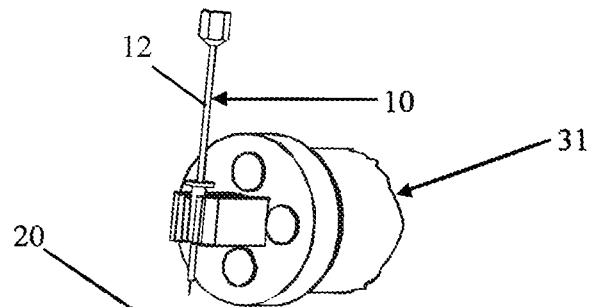
Figure 6G:
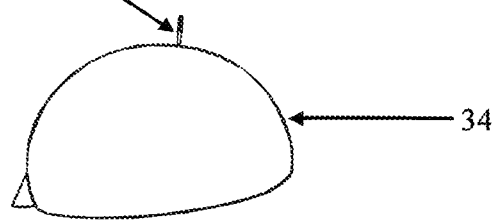
Figure 6G:
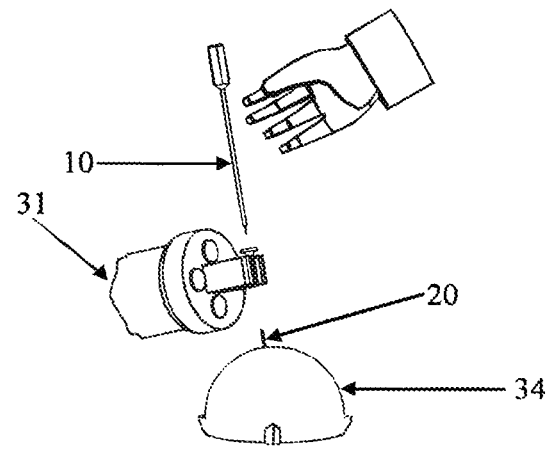

FIG. 2 shows the terminal end of shaft 12 having socket 17 and pin structure 13 extending axially therethrough. The pin structure 13 is shown protruding from the rear wall 41 of the cavity forming socket structure 17. FIG. 2A is an enlarged view of bend 16 of the pin structure 13. FIGS. 3 and 4 show anchor bolt 20 having threads 24 at one end and a formed end portion 23 at the opposite end for receiving socket 17 of the anchor bolt driver device 10. FIG. 5 shows a plurality of anchor bolts 20 threaded and positioned into the skull 23 of a patient. FIGS. 6A-6G show the utilization of the anchor bolt driver device 10 in connection with the adjusted bushing of a stereotactic frame 31.

Referring to FIGS. 3 and 4, an anchor bolt 20 is shown having a body member 21 with a lumen 22 therethrough. Threads 24 and 25 are shown disposed at the terminal ends of body member 21 which may have a length of 15 to 25 mm, for example. One end of the body member 21 is shown having a drivehead or formed end portion 23, i.e., 1 to 2 mm in length and having a square cross section for engagement by the socket 17 of the driver device 10 of the present invention.

Referring further to FIGS. 1-5, the anchor bolt driver 10 of the invention has a pin structure 13 having a predetermined shaped pin structure 13 extending axially or centrally from the socket portion 17. The anchor bolt 20, as shown in FIGS. 3 and 4, is held on the anchor bolt driver device 10 when the lumen 22 of the anchor bolt body 21 is slid onto the pin structure 13 and the formed terminal end portion 23 of the anchor bolt body 21 is pushed into the socket portion 17 of the shaft of the driver device 10. The socket portion 17 is a hollow opening or formed cavity in the terminal end of shaft 12 and may be square in shape but may also be shaped of a hex 38, starburst 39, or triangular shape 40 in cross section, as shown in FIGS. 2D, 2E and 2F depending upon the end configuration of the anchor bolt with which it is utilized. The formed terminal end portion 23 of the anchor bolt 20 is held within the socket 17 by means of the forces of the undulated portion 19 of the pin 13 springing out of shape slightly since the amplitude 18 of the bends 16 provide an undulated portion 19 that is slightly larger than the radius of the lumen 22 of the anchor bolt 20 or skull screw with inner lumen 22. The pin structure 13 with an undulated portion 19, having bends 16 is shown spaced outwardly from formed socket 17 and is designed and structured to hold the anchor bolt in place securely even if the drive head 23 of the anchor bolt 20 is not engaged with the drive socket 17 of the driver device 10. The undulated portion 19 may have at least two opposing bends 16. The pin structure 13 with undulated portion 19 and extending axially through and from socket portion 17, is also designed so the anchor bolt's linear axis is concentric with the shaft 12 of the anchor bolt driver 10. This structure is ideal for keeping the trajectory of the anchor bolt 20 in line with the angle in which the burr hole in the skull was drilled, as will be further discussed below with respect to FIGS. 6A-6G.

Figure 2B:
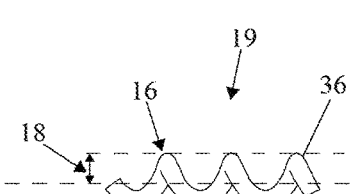
FIGS. 2B and 2C show alternate embodiments of the anchor bolt driver pin member.
Figure 2C:
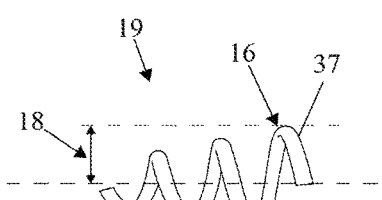
Figure 2D:
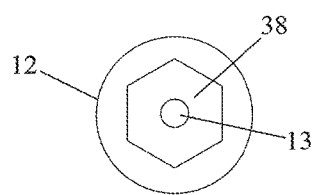
FIGS. 2D, 2E and 2F show alternate embodiments of the drive socket of the anchor bolt driver device.
Figure 2E:
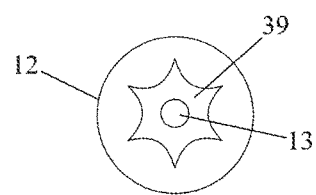
Figure 2F:
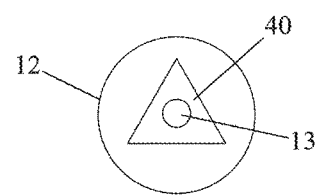

Although FIG. 1 shows an anchor bolt driver 10 with a pin structure 13 that has an undulated portion 19 with a shape similar to a sine wave, other shapes such as a helix 37 (conical spiral/helix), corkscrew 36 (cylindrical spiral/helix), a singular bend may also be utilized to hold an anchor bolt 20 with an inner lumen in place, as shown in FIGS. 2B and 2C, for example. The important aspect of the pin structure 13 being the amplitude 18 of the bend or bends 16 in the undulated portion 19 of the pin structure 13 as well as the composition of the pin structure to provide shape memory.

FIGS. 6A-6G show the anchor bolt driver device 10 of the invention being directed through bushing 32 of the stereotactic frame 31 and towards a burr hole in the depiction of a skull 34. As shown in FIGS. 6A-6G, once a burr hole has been drilled into the skull, also utilizing the stereotactic frame, the anchor bolt driver device 10 having an anchor bolt 20 attached thereto is extended through the lumen of the adjusted bushing of the stereotactic frame 31. The bushing 32 having a lumen, permits the anchor bolt 20, by means of the bolt driver device 10, to engage the burr hole 35 in the skull 34.

The anchor bolt driver 10 is a reusable tool that can be sterilized via STERRAD or steam autoclaving. The shape of the pin structure 13 allows for ease of cleaning using a cleaning wipe and the anchor bolt driver is a one piece, unitary design. The anchor bolt driver's shaft 12 may have any desired length and having a similar diameter as the anchor bolt 20 and the drill bit used to create the burr hole in the skull of a patient. The latter allows the same size stereotactic lumen to accept the introduction and passing through of these three items. This speeds up the process of the surgery, thereby saving money since time in the operating room is very expensive. The alternative would be to alternate between different bushings with different lumens or to utilize a reducing bushing to add and remove in the drilling process. The latter, however, adds time and could also reduce the accuracy of the stereotactic procedure.

Referring to FIGS. 5 and 6A-6G, the stereotactic procedure using the anchor bolt driver 10 of the invention consists of the following steps:

1. Drilling a hole in the patient's skull 28 (skull depiction 34) by first placing the drill through the lumen of the stereotactic bushing 32.
2. Removing the drill from the bushing.
3. Pushing the anchor bolt 20 onto the anchor bolt driver's pin 13 until the drive head 23 on the anchor bolt 20 is mating with the drive socket 17 of the driver device 10.
4. Inserting the anchor bolt driver 10 with the anchor bolt 20 attached through the lumen of the stereotactic bushing and screwing the self tapping anchor bolt into the skull. (Hand 33 is shown turning the driver device 10.)

5. Pulling out the anchor bolt driver device 10 from the lumen of the stereotactic bushing. This process also disengages the socket from the drive head of the anchor bolt.

As shown in FIG. 5, anchor bolts 20 are positioned in skull 28, having caps 29 and through which electrode leads 30 extend.

In forming the shaped pin portion 13 of the driver device 10, a length of nitinol wire is placed in a stainless steel mandrel that holds the wire to a predetermined shape. As heat is applied to the nitinol wire and taken away, the nitinol wire keeps the shape of the mandrel when it is taken out of the mandrel. The shaft 12 of the driver device 10 may have a machined or forged socket 17 having a rear wall 41 with a blind hole 42 for soldering the pin structure 13 in place at connection 15, for example. The handle portion 10 may be fixed at connection 14, i.e., soldered, to the shaft 12.

Another embodiment of the invention is to have the pin structure 13 and the handle pinned in place or having a set screw fixating these elements in place by means of a screw perpendicular to the axis of the pin or drive shaft.

It is within the purview of the invention to provide the driver device as part of a socket bit attachable to an electronic driver or other driver structure. As shown in FIG. 2A, the amplitude 18 of bend 16 is dependent upon the size of bone screw's or anchor bolt's inner lumen. The driver device 10 is preferably constructed of a rust-proof material such as 300 series stainless steel. The pin structure 13 may be constructed of a spring wire material such as stainless steel, a shape memory alloy such as nitinol or like material.

As many changes are possible to the anchor bolt driver device embodiments of this invention utilizing the teachings thereof, the descriptions above, and the accompanying drawing should be interpreted in the illustrative and not in the limited sense.

That which is claimed is:

1. An anchor bolt driver device for use in a stereotactic frame and for engaging the formed terminal driver end of an anchor bolt having a lumen therethrough comprising;
   a) a handle portion,
   b) a shaft extending axially from said handle portion, said shaft having a terminal end, said terminal end of said shaft having a cavity therein, said cavity being formed into a socket having a predetermined cross sectional configuration for engaging the terminal driver end of the anchor bolt and wherein said shaft of said anchor bolt driver device is constructed and arranged to be used through a lumen of a bushing of the stereotactic frame, and,
   c) an elongated unitary and formed pin structure for engaging the lumen of the anchor bolt, said pin structure extending through and from said cavity in said terminal end of said shaft and extending axially outward through said socket of said shaft, said pin structure having an axially aligned distal end and at least two spatially opposing bends with an amplitude of a predetermined dimension, said at least two spatially opposing bends of said pin structure being spaced outwardly from said terminal end of said shaft, whereby said at least two bends of said pin structure holds the anchor bolt within its lumen and wherein said socket of said shaft of said anchor driver device engages the formed terminal end of the anchor bolt to turn the anchor bolt and to accurately position the anchor bolt into the skull of a patient by means of the stereotactic frame.

2. The anchor bolt driver device of claim 1, wherein said socket formed by said cavity in said terminal end of said pin structure has a rear wall with a centrally disposed hole and wherein said elongated unitary and formed pin structure is secured within said hole and extends outwardly through said socket.

3. The anchor bolt driver device of claim 1, wherein said elongated and formed pin structure is constructed of a shape memory metal.

4. The anchor bolt driver device of claim 3, wherein said shape memory metal is nitinol or spring steel.

5. The anchor bolt driver device of claim 1, wherein said socket of said shaft has a cross sectional configuration selected from the configurations consisting of a square, hexagonal, star burst and a triangular configuration.

6. The anchor bolt driver device of claim 1, wherein said elongated and formed pin structure has a shape selected from the shapes consisting of a sinewave, a conical helix, and a corkscrew shape.

7. The anchor bolt driver device of claim 1, wherein said amplitude of said at least two bends is larger than a radius of the lumen of the anchor bolt or skull screw for which said anchor bolt driver device is used.

8. A unitary anchor bolt driver device for threading an anchor bolt having a lumen into the skull of a patient, said anchor bolt driver comprising;
   a) a handle portion,
   b) a shaft extending axially from said handle portion, said shaft having a terminal end with a cavity formed into a socket having a predetermined cross sectional configuration, and
   c) a single elongated unitary and formed pin structure extending from said cavity of said terminal end of said shaft and extending outward through said socket, said pin structure having an undulated portion having at least two spatially opposing bends spaced outwardly from said socket, said undulated portion having an amplitude of a predetermined dimension and wherein said elongated and formed pin structure is constructed of a shape memory metal, said at least two bends constructed and arranged to engage the lumen of the anchor bolt.

9. The unitary anchor bolt driver device of claim 8, wherein said shape memory metal is nitinol or spring steel.

10. The unitary anchor bolt driver device of claim 8, wherein said socket of said shaft has a cross sectional configuration selected from the configurations consisting of a square, hexagonal, star burst and a triangular configuration.

11. The unitary anchor bolt driver device of claim 8, wherein said undulated portion of said elongated and formed pin structure has a shape selected from the shapes consisting of a sinewave, a conical helix, and a corkscrew shape.

12. The unitary anchor bolt driver device of claim 8, wherein said predetermined dimension of said amplitude of said undulated portion is larger than a radius of the lumen of the anchor bolt or skull screw for which said anchor bolt driver device is used.

13. The unitary anchor bolt driver device of claim 8, wherein said shaft of said anchor bolt driver device has a length and a diameter constructed for use through a lumen of a bushing of a stereotactic device and wherein said shaft diameter is approximately equal to the diameter of the anchor bolt and a drill bit used to create a burr hole in the skull of a patient.

14. An anchor bolt socket and holding device for threading an anchor bolt or skull screw into the skull of a patient, the anchor bolt or skull screw having a lumen and a terminal end of a predetermined configuration, said anchor bolt socket and holding device comprising;

a) a shaft for engagement with a driver device, said shall having a terminal end formed into a socket having a predetermined cross sectional configuration for engaging the terminal end of the anchor bolt or skull screw, and b) an elongated unitary and formed pin structure extending from said terminal end of said shaft and extending outward through said socket, said elongated and formed pin structure being constructed and arranged for entry into the lumen of the anchor bolt or skull screw, said pin structure having an undulated portion with at least two spatially opposing bends, said undulated portion having an amplitude of a predetermined dimension, said undulated portion being spaced outward from said socket, wherein said amplitude of said undulated portion is larger than a radius of the lumen of the anchor bolt or skull screw for which the socket of said shaft is used and wherein said elongated and formed pin structure has a shape selected from the shapes consisting of a sinewave, a conical helix, and a corkscrew shape.

15. The anchor bolt socket and holding device of claim 14, wherein said elongated and formed pin structure is constructed of a shape memory metal.

16. The anchor bolt socket and holding device of claim 15, wherein said shape memory metal is nitinol or spring steel.

17. The anchor bolt socket and holding device of claim 14, wherein said cross sectional configuration of said socket of said shaft is selected from the configurations consisting of a square, hexagonal, star burst and a triangular configuration.

18. The anchor bolt socket and holding device of claim 14, wherein a handle member is attached to said anchor bolt socket and holding device.

19. The anchor bolt socket and holding device of claim 14, wherein said anchor bolt socket and holding device is a socket bit.

20. The anchor bolt socket and holding device of claim 14, wherein said shaft of said anchor bolt socket and holding device is constructed and arranged to be used through a lumen of a bushing of a stereotactic device.

* * * * *